United States Patent [19]

Torii et al.

[11] Patent Number: 4,501,730

[45] Date of Patent: Feb. 26, 1985

[54] DEODORANT COMPOSITIONS

[75] Inventors: Kuniyoshi Torii; Chikashi Egma, both of Shiga, Japan

[73] Assignee: Shiraimatsu Shinyaku Company Ltd., Japan

[21] Appl. No.: 621,889

[22] Filed: Jun. 19, 1984

Related U.S. Application Data

[63] Continuation of Ser. No. 407,786, Aug. 13, 1982, abandoned.

[30] Foreign Application Priority Data

Oct. 9, 1981 [JP] Japan ................................ 56-161796

[51] Int. Cl.$^3$ ........................ A61L 13/00; A61K 35/78
[52] U.S. Cl. .................................... 424/76; 424/195.1
[58] Field of Search .................................. 424/76, 195

[56] References Cited

PUBLICATIONS

Tanabe, Odour Combating Compositions, 1978, Chem. Abst. 89:185921e.

Primary Examiner—Albert T. Meyers
Assistant Examiner—John W. Rollins
Attorney, Agent, or Firm—Wenderoth, Lind & Ponack

[57] ABSTRACT

Potent, long acting deodorant compositions are produced from isolates of the theaceae plant which isolates are produced by dry-distillation of all or a part of said plant.

3 Claims, No Drawings

DEODORANT COMPOSITIONS

This application is a continuation of now abandoned application Ser. No. 407,786, filed Aug. 13, 1982, now abandoned.

BACKGROUND AND PRIOR ART

This invention relates to the provision of potent and long acting deodorant compositions containing, as an active ingredient, isolates from theaceae plants. More particularly, it relates to deodorant compositions containing isolates which are obtained by dry-distillation mainly from leaves of the theaceae plant, which isolates are refined to the extent to exhibiting fixed properties.

It has been known that leaves and the other parts of theaceae plants such as *Thea sinensis, Camellia japonica, Cleyera ochnaceae* and *Eurya japonica* have a deodorant effect and one of the present inventors and his collaborators disclosed in Japanese Non-examined Patent Publication Gazette No. 66434/1978 deodorant compositions containing as an active ingredient a crude and colored substance extracted from theaceae plants; however, little was disclosed in said Japanese publication relating to physical and chemical properties of the active ingredient.

Further, because this process was carried out by extracting raw materials with solvents such as water, alcohols, ketones and isopropanol under reflux, the extracts were not as effective for deodorization as the active ingredient of the present invention.

BRIEF SUMMARY

The present invention provides an extract effective for deodorization by subjecting theaceae plants or portions thereof to dry-distillation.

DETAILED DESCRIPTION

In accordance with this invention, the dry-distillation can be conducted at a reduced pressure of 20 mm/Hg and effluents having the boiling point between 180°–200° C. are collected. The effluents are pale yellow or pale brown and are aromatic liquids, which instantly become viscous on exposure to air. Thus, it is recommended to deposit them in an inert solvent such as propylene glycol. If the distillation temperature exceeds 200° C. at a reduced pressure of 20 mm/Hg, it is likely to cause decomposition of the active ingredient.

The present invention will be more fully understood with reference to the following specific embodiments:

EXAMPLE 25 kilograms of raw leaves of a Chinese tea tree, *Thea sinensis*, were subjected to dry-distillation under a reduced pressure of 20 mm/Hg in a dry-distillation oven and the effluents having the boiling point between 180°–200° C. were collected in propylene glycol. The yield of the thus prepared distillates was 50 grams, and the distillation was a pale yellow liquid.

The active ingredient of this invention is a pale yellow or pale brown, oily and aromatic liquid and has slightly sweet taste. It is soluble in water and other polar solvents such as alcohols and organic acetates and is insoluble in benzene, toluene and xylene.

Physical properties of the active ingredient of this invention has been determined as follows:

Boiling point: 180°–200° C. (at 20 mm/Hg)

Refractive index: $n_D^{20} = 1.418 \pm 0.02$ (in 20 w/w% propylene glycol solution)

Angle of optical rotation: $\alpha_D^{20} = +0.007° \pm 0.002°$ (in 20 w/w% propylene glycol solution)

Specific gravity: $d_{20}^{20} = 1.025 \pm 0.02$ (in 20 w/w% propylene glycol solution)

The 1.000 times by weight water solution of the active ingredient in 20 w/w% propylene glycol exhibits an ultraviolet absorption spectrum maximum peak at $276 \pm 2$ m$\mu$.

The constituents of the active ingredient of this invention have not been definitely clarified, however, they are presumed to consist of flavanols, flavonols and other organic higher molecules. Their deodorant effectiveness may be due to a complex mechanism consisting of clathrating, addition and neutralization reactions with the active ingredient of malodorous sources in addition to biological reactions in human beings, such as inhibition of olfactory receptors.

An example of the deodorant effect of the active ingredient of this invention is indicated by a following experiment:

Malodorous substance:
28% Ammonia
Trimethylamine
Hydrogen sulfide
Methylmercaptan
Standard solution:
20 w/w% propylene glycol solution of the active ingredient.
Method:

Each of the malodorous substances is adjusted to a fixed concentration into a closed vessel (5.000/ml.) together with one gram of the standard solution, and the vessel is kept at a room temperature. After every 1, 3, 5, 10 and 20 minutes, the free gas remaining in the vessel is removed and the total weight of the free gas is quantitatively determined through a neutralization by titration method with acid or alkali depending on the type of gas, with the exception of hydrogen sulfide which is quantitatively determined by an iodometry titration of sodium hydroxide solution.

Result:

| Malodorous substance | Concentration (ppm) at Beginning | % of Reduced Weight of Free Gas Minutes | | | | |
|---|---|---|---|---|---|---|
| | | 1 | 3 | 5 | 10 | 20 |
| 28% Ammonia | 3000 | 84 | 98 | 100 | 100 | 100 |
| Trimethylamine | 1898 | 66 | 90 | 98 | 100 | 100 |
| Hydrogen sulfide | 861 | 12 | 23 | 31 | 47 | 100 |
| Methylmercaptan | 50 | 23 | 38 | 64 | 75 | 86 |

The value of acute toxicity ($LD_{50}$) of the standard solution of the active ingredient of this invention has been determined to be more than 30 ml. per kilogram of a body weight on male and female rats. Consequently, it is very low in toxicity.

The standard solution of the active ingredient of this invention can be formulated for deodorant uses in various forms with the aid of excipients, adjuvants and additives known in the art depending on the location and the purpose of application, some of which are illustrated as follows:

Granules:
The standard solution: 10 parts by weight

Lactose: 75 parts by weight
Dextrin: 15 parts by weight

These components are kneaded with water and are molded by a conventional method.

Tablets:
The standard solution: 10 parts by weight
Lactose: 75 parts by weight
Dextrin: 10 parts by weight
Talc: 5 parts by weight These components are made into tablets according to a conventional method.

Aerosols:
The standard solution: 40 parts by weight
Dichlorofluoromethane: 500 parts by volume
Perfume: optional The above components are filled into aerosol cans according to a conventional method.

Solid preparation:
10 parts by weight of the standard solution are diluted with 10 times by volume of alcohol and 150 parts by weight of several pieces of an unglazed plate are soaked therein for 10 minutes. The pieces are taken out and are substantially dried.

Fumigation preparations:
The standard solution: 5 parts by weight
Powdered charcoal: 85 parts by weight
Carboxymethylcellulose: 0.5 parts by weight
Powdered perfume: 9.5 parts by weight The above components are kneaded and molded into granules.

The thus produced variety of preparations are applicable for deodorization of water and other malodorous sources and are applied to, for example, refrigerators, lavatories, dust disposal bins, fishing boats, stockyards, food storage areas and the like. An effective dose of the standard solution depends, of course, upon the weight and kind of malodorous sources and other surrounding circumstances, however, it is tentatively recommended to employ 0.01–0.1% by weight of the standard solution for a given weight of malodorous substance.

We claim:

1. A deodorant distillate produced by a process which comprises dry-distillation of the leaves of Thea sinensis, said distillate having a boiling point of 180°–200° C. (at 20 mm/Hg) and exhibiting the following properties in a 20 w/w% propylene glycol solution:

| | |
|---|---|
| Refractive index | $n_D^{20} = 1.418 \pm 0.02$ |
| Angle of optical rotation | $\alpha_D^{20} = 0.007° \pm 0.002°$ |
| Specific gravity | $d_{20}^{20} = 1.025 \pm 0.02$ |
| Ultraviolet absorption maximum peak | $276 \pm 2$ m$\mu$ (20 w/w % propylene glycol solution diluted by water in the amount of 1.000 times the weight of said solution). |

2. The distillate according to claim 1, said dry-distillation is carried out at a temperature not exceeding 200° C. at a reduced pressure of 20 mm/Hg.

3. A deodorizing composition which comprises an effective amount of the distillate of claim 1, in the form of a 20 w/w% propylene glycol solution.

* * * * *